(12) United States Patent
Rundo et al.

(10) Patent No.: US 11,471,084 B2
(45) Date of Patent: Oct. 18, 2022

(54) IMAGE PROCESSING METHOD AND CORRESPONDING SYSTEM (71) Applicant: STMicroelectronics S.r.l., Agrate Brianza (IT)

(72) Inventors: Francesco Rundo, Gravina di Catania (IT); Francesca Trenta, Camporotondo Etneo (IT); Sabrina Conoci, Tremestieri Etneo (IT); Sebastiano Battiato, Aci Catena (IT)

(73) Assignee: STMicroelectronics S.R.L., Agrate Brianza (IT)

( * ) Notice: Subject to any disclaimer, the term of this patent is extended or adjusted under 35 U.S.C. 154(b) by 395 days.

(21) Appl. No.: 16/729,879

(22) Filed: Dec. 30, 2019

(65) Prior Publication Data
US 2020/0214614 A1 Jul. 9, 2020

(30) Foreign Application Priority Data
Jan. 7, 2019 (IT) .................. 102019000000133

(51) Int. Cl.
G01C 22/00 (2006.01)
A61B 5/18 (2006.01)
(Continued)

(52) U.S. Cl.
CPC .............. A61B 5/18 (2013.01); A61B 5/0255 (2013.01); A61B 5/02405 (2013.01);
(Continued)

(58) Field of Classification Search
CPC ... A61B 5/18; A61B 5/02405; A61B 5/02416; A61B 5/0255; A61B 5/6893;
(Continued)

(56) References Cited

U.S. PATENT DOCUMENTS 10,748,016 B2 * 8/2020 Hutchinson .......... A61B 5/7207
2013/0345568 A1 12/2013 Mestha et al.
(Continued)

FOREIGN PATENT DOCUMENTS

WO 2015174963 A1 11/2015

OTHER PUBLICATIONS

Radha, Mustafa, et al., "Estimating blood pressure trends and the nocturnal dip from photoplethysmography", XP081432154, Oct. 2018, 20 pages.

*Primary Examiner* — Anh V La
(74) *Attorney, Agent, or Firm* — Slater Matsil, LLP (57) ABSTRACT A method includes receiving a video signal that comprises a time series of images of a face of a human, wherein the images in the time series of images comprise a set of landmark points in the face, applying tracking processing to the video signal to reveal variations over time of at least one image parameter at the set of landmark points in the human face, generating a set of variation signals indicative of variations revealed at respective landmark points in the set of landmark points, applying processing to the set of variation signals, the processing comprising artificial neural network processing to produce a reconstructed PhotoPletysmoGraphy (PPG) signal, and estimating a heart rate variability of a variable heart rate of the human as a function of the reconstructed PPG signal.

20 Claims, 6 Drawing Sheets (51) Int. Cl.

| | |
|---|---|
| *B60W 60/00* | (2020.01) |
| *A61B 5/024* | (2006.01) |
| *A61B 5/0255* | (2006.01) |
| *A61B 5/00* | (2006.01) |
| *B60W 40/08* | (2012.01) |
| *B60W 50/14* | (2020.01) |
| *G06N 3/04* | (2006.01) |
| *G06N 3/08* | (2006.01) |
| *G06V 20/59* | (2022.01) |
| *G06V 40/16* | (2022.01) |
| *G06K 9/62* | (2022.01) |

(52) U.S. Cl.
CPC ........ *A61B 5/02416* (2013.01); *A61B 5/6893* (2013.01); *A61B 5/6898* (2013.01); *A61B 5/7267* (2013.01); *A61B 5/7278* (2013.01); *A61B 5/746* (2013.01); *B60W 40/08* (2013.01); *B60W 50/14* (2013.01); *B60W 60/0051* (2020.02); *G06N 3/0445* (2013.01); *G06N 3/08* (2013.01); *G06V 20/597* (2022.01); *G06V 40/165* (2022.01); *G06V 40/166* (2022.01); *G06V 40/167* (2022.01); *A61B 5/0077* (2013.01); *A61B 2576/02* (2013.01); *B60W 2050/143* (2013.01); *G06K 9/6262* (2013.01); *G06N 3/0454* (2013.01)

(58) Field of Classification Search
CPC ... A61B 5/6898; A61B 5/7267; A61B 5/7278; A61B 5/746; A61B 5/0077; A61B 2576/02; B60W 40/08; B60W 50/14; B60W 60/0051; B60W 2050/143; B60W 2420/42; B60W 2540/229; G06N 3/0445; G06N 3/08; G06N 3/0454; G06N 5/003; G06N 20/20; G06N 3/0481; G06V 20/597; G06V 40/165; G06V 40/166; G06V 40/167; G06V 40/171; G06V 40/15; G06K 9/6262
USPC ................. 701/23; 340/573.1, 439, 457, 576
See application file for complete search history.

(56) References Cited

U.S. PATENT DOCUMENTS

| | | | |
|---|---|---|---|
| 2015/0099987 A1 | 4/2015 | Bhatkar et al. | |
| 2015/0328985 A1* | 11/2015 | Kim | A61B 5/163 180/272 |
| 2016/0345907 A1* | 12/2016 | Fung | G06K 9/00536 |
| 2019/0087690 A1* | 3/2019 | Srivastava | G06F 1/3296 |
| 2019/0099118 A1* | 4/2019 | Patel | G07C 5/008 |
| 2019/0213429 A1* | 7/2019 | Sicconi | G06F 3/0346 |
| 2019/0391581 A1* | 12/2019 | Vardaro | A61B 5/02055 |
| 2019/0392235 A1* | 12/2019 | Shimizu | H04W 4/40 |

* cited by examiner

IMAGE PROCESSING METHOD AND CORRESPONDING SYSTEM

CROSS-REFERENCE TO RELATED APPLICATIONS

This application claims priority to Italian Patent Application No. 102019000000133, filed on Jan. 7, 2019, which application is hereby incorporated herein by reference.

TECHNICAL FIELD

The description relates to techniques for image processing.

BACKGROUND

Driver's drowsiness may cause serious road traffic accidents involving vehicles. The possibility to detect an attention state of a driver, for instance in the automotive field, may facilitate evaluation of his/her fitness to drive a vehicle, facilitating to prevent road accidents.

Computer vision systems may be integrated in vehicles, e.g., equipped with advanced driver assistance systems, briefly ADAS, in order to alert the driver in the occurrence of detected deviations from a road lane. Methods based on detecting lane deviations, nevertheless, may fail in alerting the driver due to suboptimal lane or environment visibility conditions (e.g., fog, snow, etc.).

Hence, an extensive activity has been carried out to provide ADAS with methods facilitating to detect the attention/drowsiness level of a driver.

For instance, it may be possible to detect an attention state, specifically based on the heart rate variability, briefly HRV.

Heart rate variability (HRV) is the physiological phenomenon of variation in the time interval between heartbeats. Thus, HRV is indicative of autonomous nervous system activity state, which is responsible of operating automatic, unconscious and involuntary body activities, such as heartbeat activity.

An HRV value may be obtained via processing of measured electrophysiological signals related to heartbeats, e.g., ECG and/or PPG signals.

Figure 1A:
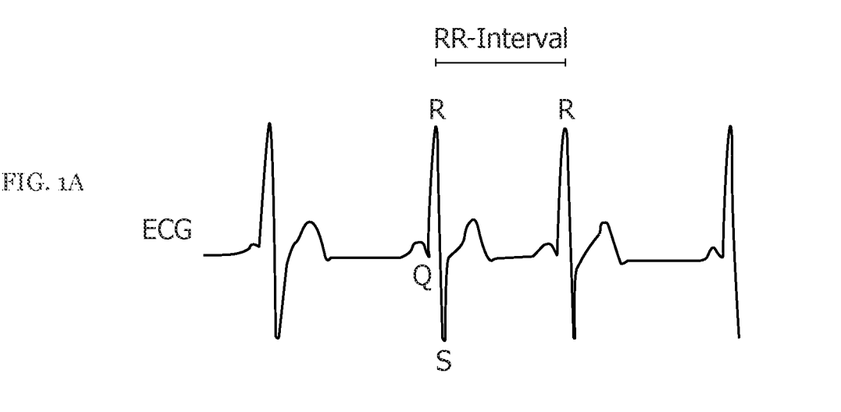
Figure 1B:
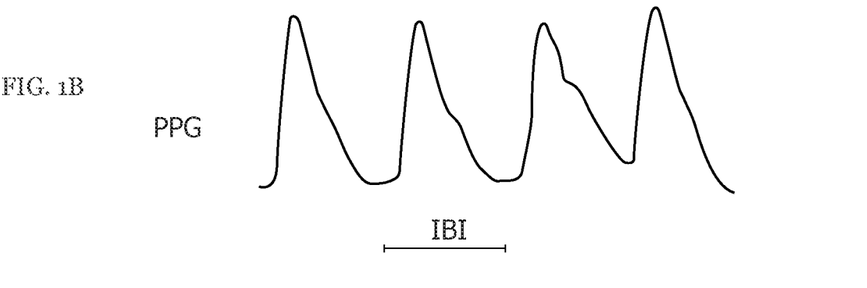

FIG. 1A is exemplary of a diagram of an ECG signal, while portion FIG. 1B is exemplary of a diagram of a PPG signal.

Using ECG, or electrocardiogram, it's typically the R peak that marks a heartbeat. Hence, the intervals between heartbeats are called R-R intervals, which may be used to compute HRV. Using PPG (PhotoPlethysmoGraphy), Inter-Beat Intervals (IBIs) may be measured to compute HRV in place of R-R intervals.

For instance, if heartbeats in a measured ECG signal have a constant period, HRV may have a low value; conversely, HRV may have a high value in an opposite case.

For instance, if the ECG signal comprises an irregular pattern of heartbeats, it may indicate that the body is in a rest condition, while if the ECG signal comprises a regular pattern of heartbeats, it may be indicative of chronic stress in the body.

ECG signals may suffer from artifacts due to motion of micro-motion of a person during signal measurement.

PPG signals may have higher tolerance than ECG signals to such motion. Moreover, PPG signals are effectively indicative of blood flow variations, facilitating to evaluate skin micro-motion otherwise imperceptible by naked eye. At the same time, integrating PPG measurement devices and systems in the compact space of a vehicle, e.g., a car, may be costly.

An extensive activity is carried on and several approaches are proposed in literature to implement driver attention detection systems. A majority of works focus on biometric data (briefly, bio-data) analysis, as discussed in the following.

Shin, Heung-Sub et al. ("Real time car driver's condition monitoring system." 2010 IEEE Sensors (2010): p. 951-954) discusses the design of ECG (Electrocardiogram) sensor with conductive fabric electrodes and PPG (Photoplethysmogram) sensor to obtain physiological signals for car driver's health condition monitoring. ECG and PPG signals are transmitted to base station connected to the server PC via personal area network for practical test. Intelligent health condition monitoring system is designed at the server to analyze the PPG and ECG signals to process HRV signals analysis derived from the physiological signals in time and frequency domain and to evaluate the driver's drowsiness status.

Koh, Sukgyu et al. ("Driver drowsiness detection via PPG biosignals by using multimodal head support." 2017 4th International Conference on Control, Decision and Information Technologies (CoDIT) (2017): p. 0383-0388) discusses a method of detecting drowsy driving that utilizes the Low Frequency (LF), High Frequency (HF), and LF/HF values of PhotoPlethysmoGraphy (PPG) signals measured on fingers and earlobes.

V. P. Nambiar, et al. ("Evolvable Block-based Neural Networks for classification of driver drowsiness based on heart rate variability," 2012 IEEE International Conference on Circuits and Systems (ICCAS), Kuala Lumpur, 2012, pp. 156-161) discusses a method to detect driver drowsiness by classifying the power spectrum of a person's HRV data using Block-based Neural Networks (BbNN), which is evolved using Genetic Algorithm (GA). BbNNs due to its regular block based structure is indicated to have relatively fast computational speeds, lower resource consumption, and equal classifying strength in comparison to other artificial neural networks (ANNs).

Sari, Nila Novita and Yo-Ping Huang ("A two-stage intelligent model to extract features from PPG for drowsiness detection." 2016 International Conference on System Science and Engineering (ICSSE) (2016): p. 1-2) discusses a two-stage intelligent model that combined the wavelet packet transform (WPT) and functional-link-based fuzzy neural network (FLFNN) to access drowsy level to develop a sensor device that detects drowsy status at an early stage.

Various solutions proposed in the literature may be exposed to one or more of the following drawbacks: costly integration of dedicated designed sensor devices for bio-data measurement in vehicles, low tolerance to measurement conditions different from ideal ones, e.g., driver not positioned correctly with respect to the sensor devices, micromotion, costly integration of complex artificial neural networks (ANNs) technologies in vehicles, good results solely as a result of big amounts of data analyzed.

SUMMARY

The description relates to techniques for image processing. For instance, such techniques may be employed in an image processing method to reconstruct electro-physiological signals to detect drowsiness of a driver.

Despite the extensive activity in the area, improved solutions facilitating, for instance, detecting a drowsy state of a vehicle driver are desirable.

A method to estimate a driver's state from PPG signals reconstructed from face landmark points in camera-recorded images may be exemplary of such a method.

One or more embodiments may relate to a corresponding system and vehicle.

One or more embodiments may relate to the method as a computer-implemented method.

One or more embodiments may comprise a computer program product loadable in the memory of at least one processing circuit (e.g., a computer) and comprising software code portions for executing the steps of the method when the product is run on at least one processing circuit. As used herein, reference to such a computer program product is understood as being equivalent to reference to computer-readable medium containing instructions for controlling the processing system in order to co-ordinate implementation of the method according to one or more embodiments. Reference to "at least one computer" is intended to highlight the possibility for one or more embodiments to be implemented in modular and/or distributed form.

One or more embodiments may comprise a Long Short-Term Memory (LSTM) artificial neural network processing for PPG prediction.

One or more embodiments may employ an optional parallel employing Convolutional Neural Network processing (CNN) for face expressions recognition to make the system robust to unexpected errors.

In one or more embodiments, the system may perform estimation of HRV value of a vehicle driver and use it to indicate driver's drowsiness/attention levels.

One or more embodiments may offer one or more of the following advantages:

providing a "sensor-less" biometric data acquisition system, facilitating evaluation of cardiac and heartbeat activity with general purpose devices, e.g. such as a smartphone equipped with a camera, providing satisfactory results while processing image frames and videos acquired with a camera with a low frame-rate, facilitating obtaining a reconstructed PPG signal from an image of a face of a person driving a vehicle, increase scalability, e.g. providing a method that can be integrated also on "old" vehicle models, employ simple neural networks for processing pixel data from one or more region of the face, hence improving accuracy in the reconstructed PPG signal.

The claims are an integral part of the technical teaching provided herein with reference to the embodiments.

BRIEF DESCRIPTION OF THE DRAWINGS

One or more embodiments will now be described, by way of non-limiting example only, with reference to the annexed Figures, wherein:

FIGS. 1A and 1B are discussed in the foregoing,

DETAILED DESCRIPTION OF ILLUSTRATIVE EMBODIMENTS

In the ensuing description, one or more specific details are illustrated, aimed at providing an in-depth understanding of examples of embodiments of this description. The embodiments may be obtained without one or more of the specific details, or with other methods, components, materials, etc. In other cases, known structures, materials, or operations are not illustrated or described in detail so that certain aspects of embodiments will not be obscured.

Reference to "an embodiment" or "one embodiment" in the framework of the present description is intended to indicate that a particular configuration, structure, or characteristic described in relation to the embodiment is comprised in at least one embodiment. Hence, phrases such as "in an embodiment" or "in one embodiment" that may be present in one or more points of the present description do not necessarily refer to one and the same embodiment.

Moreover, particular conformations, structures, or characteristics may be combined in any adequate way in one or more embodiments.

The references used herein are provided merely for convenience and hence do not define the extent of protection or the scope of the embodiments.

Throughout the instant description of ordinal numbers, (e.g. first, second, third, . . . ) will be used with the purpose of facilitating the identification of components. It will be otherwise appreciated that such ordinal numbers are merely intended for that purpose and shall not be construed, even indirectly, in a limiting sense of the embodiments.

Figure 2:
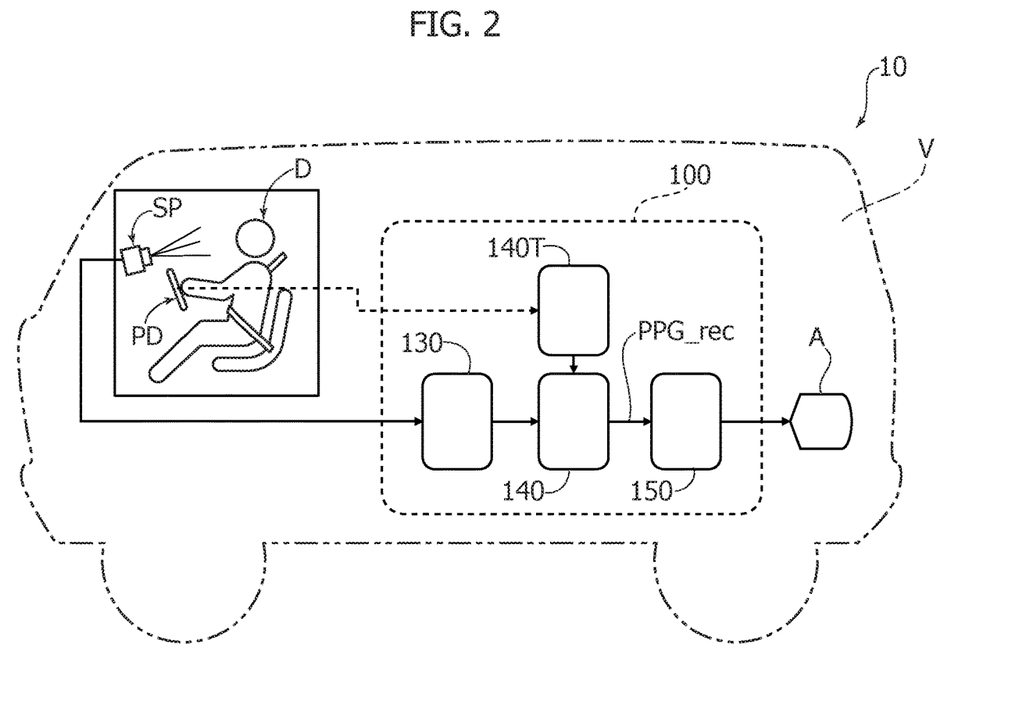
FIG. 2 is a diagram exemplary of a system as per the present disclosure.

By way of general reference, FIG. 2 is exemplary of a vehicle V comprising a system 10 for detecting a level of attention of a driver D, e.g. between wakeful or drowsy state. A camera SP, for instance a smartphone camera or a low frame rate camera, is configured to record a video. The camera SP may be configured to record images of a face of a person D driving the vehicle V, e.g., the camera may be directed towards the face of the driver D so as to record the face expressions or other body features of the driver D.

A processing pipeline 100 is coupled to the camera SP and configured to receive therefrom and process the (recorded) video signal, in order to provide an indicator signal A, e.g. the Heart Rate Variability Index (HRV) from a PPG signal. The HRV is indicative of an attention state of the driver D.

In one or more embodiments, the system 10 may comprise an Advanced Driver Assistance System (ADAS), configured to receive the indicator A and to use it in assisting the car driving operations, for instance providing an alert to the driver D of the vehicle V as a result of the indicator A being below or above a certain threshold and/or taking control over the vehicle in case a drowsy driver state is detected, potentially improving driving safety.

One or more embodiments thus address the issues related to discovering possible drowsiness of the driver D (before and during the driving) starting from heart rate variability HRV estimation effected reliably on board a vehicle V.

In one or more embodiments, the camera may be a 25 fps (frame per second) video-camera.

The block diagram of FIG. 2 includes one or more PPG probes PD. For instance, the platform as exemplified herein can include a coupled LED-Silicon photomultiplier (SiPM) detector, e.g., silicon SiPM's with a total area of 4.0×4.5 mm2 and 4871 square microcells with 60 micron (1 micron=10-6 m) pitch along with OSRAM LT M673 LEDs in SMD package emitting at two selected wavelengths.

Figure 6:
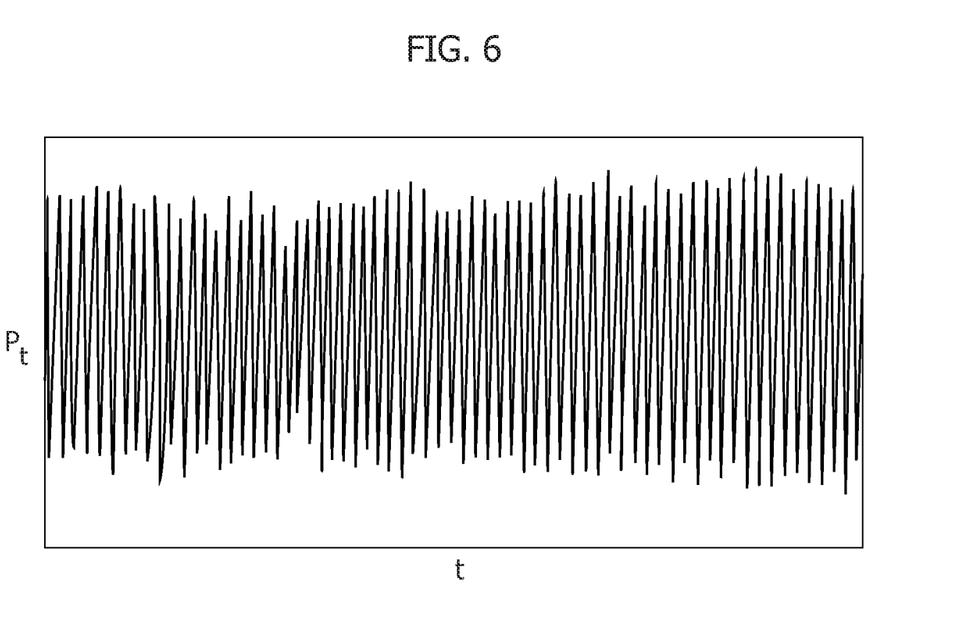

In one or more embodiments, the system may comprise a stage of acquiring a PPG signal Pt of the car driver D for preliminary system 100 calibration and/or for real time continuous learning, as discussed in the following, e.g. the PPG signal Pt being sampled by car probes PD placed on the steering wheel (see, for instance, FIG. 6).

In one or more embodiments, the processing pipeline 100 may comprise an image pre-processing stage 130, coupled to the camera SP and configured to process data received therefrom in order to provide time-series of variation of luminance/intensity of points or areas of the video-frames in the video, as discussed in the following. An Artificial Neural Network (briefly, ANN) processing stage 20 is coupled to the pre-processing stage 130 and configured to receive the time-series therefrom and apply processing to the time-series in order to provide a reconstructed PPG signal PPG_rec.

A post-processing stage 150 is configured to receive the reconstructed PPG signal PPG_rec and process it so as to obtain the indicator A of the attention state of the driver D, e.g. the HRV value from the reconstructed PPG signal PPG_rec, which may be computed from the interval between PPG signal minimum points (IBI). A training data collection stage 140T is coupled to the ANN stage 140 and is configured to collect, store and provide training data to the ANN, as discussed in the following.

Figure 3:
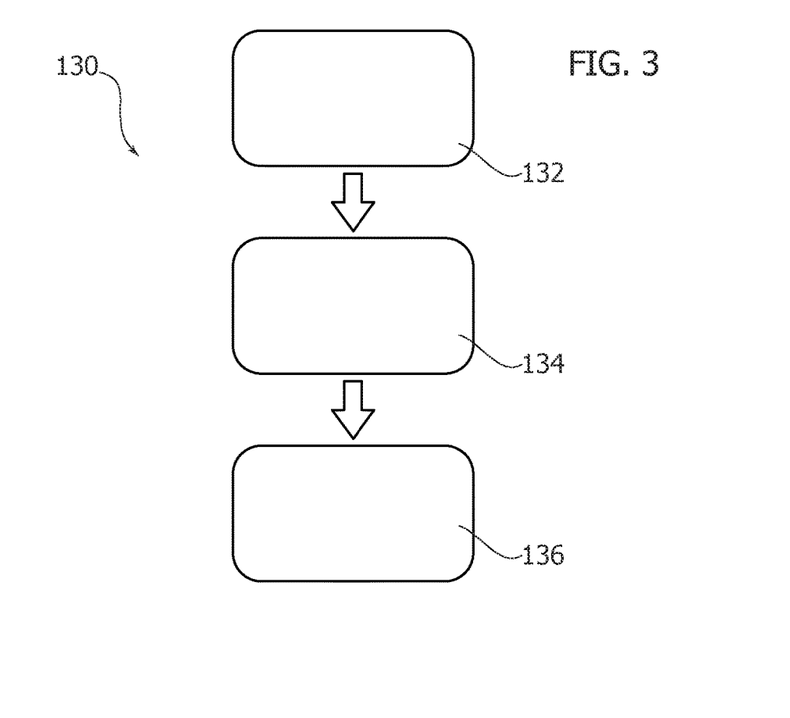
FIG. 3 is a diagram exemplary of operations in a method as per the present disclosure.

FIG. 3 is exemplary of possible sub-stages which may be employed in applying image pre-processing 130.

In one or more embodiments, pre-processing 130 may facilitate tracking face landmark points across face images in the video signal of the driver D and extracting time-series of respective image pixel intensity variation, as discussed in the following.

For instance, the image pre-processing stage 130 may comprise a first sub-stage 132, configured to extract video frames in the received video signal from the camera SP and detect a set of face landmark points, e.g. fiducial face landmark points around face components and face contour which facilitate to capture the rigid and non-rigid face deformations due to head movements and face expressions, which can be found for instance around the nose, the mouth and the eyes. A second sub-stage 134 is configured to calculate the landmarks points intensities, generating a set of time-series, e.g. comprising a time-series of luminance/intensity data for a respective face landmark point, for instance to obtain a sequence of values of intensity variations frame-by-frame, e.g. relative variation of intensity in a frame with respect to the precedent frame.

It is noted that while such sub-stages 132, 134, 136, are discussed as separate stages in the following, in one or more embodiments the sub-stages 132, 134, 136 may be incorporated, e.g., in a single pre-processing stage 130 performing the set of operations in the sub-stages 132, 134, 136.

Figure 4A:
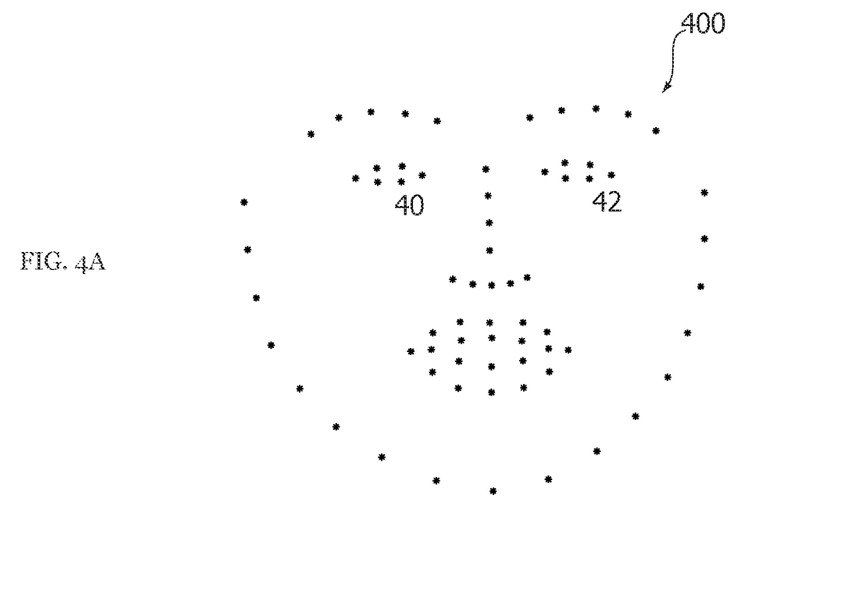
FIGS. 4A, 4B and 4C are exemplary of landmarks and respective signals.

FIG. 4A is exemplary of a set of landmark points 40, 42 in a human face 400 which may be detected in the first sub-stage 132, e.g., comprising a first landmark point 40 and a second landmark point 42.

In one or more embodiments, a face landmark detector processing may be used to map to facial structures on the face 400 in the first sub-stage 132 in the image pre-processing stage 130. For instance, a face landmark detector processing such as the one disclosed in document Kazemi, et al.: "One millisecond face alignment with an ensemble of regression trees", 2014, IEEE Conference on Computer Vision and Pattern Recognition (2014), 1867-1874 may be suitable for use in the first sub-stage 132 in the image pre-processing stage 130.

Such document discusses the problem of Face Alignment for a single image and shows how an ensemble of regression trees can be used to estimate the face's landmark positions directly from a sparse subset of pixel intensities, achieving super-realtime performance with high quality predictions. The document presents a general framework based on gradient boosting for learning an ensemble of regression trees that optimizes the sum of square error loss and naturally handles missing or partially labelled data, using appropriate priors to exploit the structure of image data, which helps with efficient feature selection. Different regularization strategies and its importance to combat overfitting are also investigated in the document, as well as the effect of the quantity of training data on the accuracy of the predictions and the effect of data augmentation using synthesized data.

For instance, the first sub-stage 132 may comprise a neural network processing trained by a training set of labeled face landmarks on an image, where the images are manually labeled, specifying specific (x, y)-coordinates of regions surrounding face structures (e.g., nose, mouth, eyes . . . ), or more specifically the probability on distance between pairs of input pixels. In the example considered, given this training data, an ensemble of regression trees is trained to estimate the face landmark positions from the intensities of image pixels (i.e., no "feature extraction" is taking place).

In one or more embodiments, hence, the first sub-stage 132 in the processing pipeline 100 comprises a face landmark detector that can be used to detect face landmarks in real-time with high quality predictions.

In one or more embodiments, the second sub-stage may generate time-series of data of intensity evolution in time for landmark points.

Figure 4B:
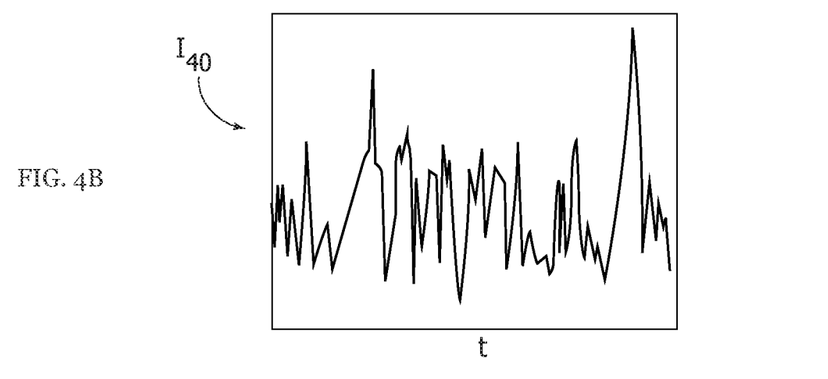
Figure 4C:
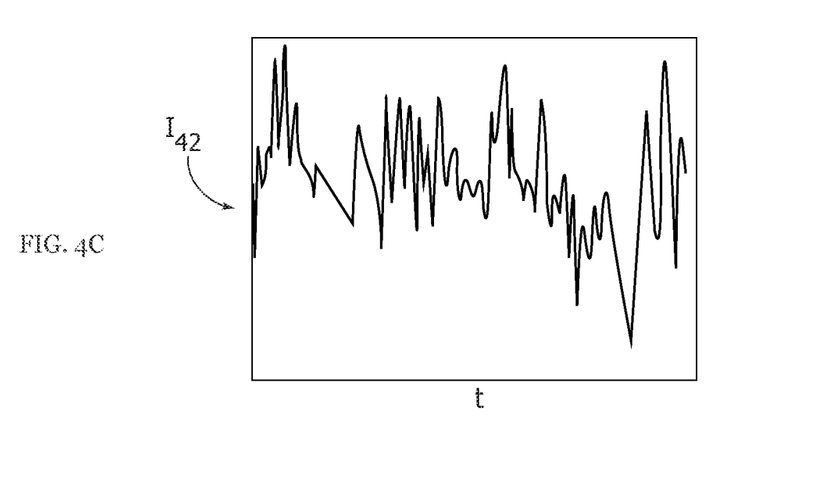

For instance, as shown in FIGS. 4B and 4C, a first time-series 140 of intensity may be associated to the first landmark point 40 and a second time-series 142 of intensity may be associated to the second landmark point 42 in the set of landmark points 400. For instance, the first time-series 140 may comprise sequential values of pixel intensities for a same pixel associated/corresponding to the respective landmark point position.

Figure 5:
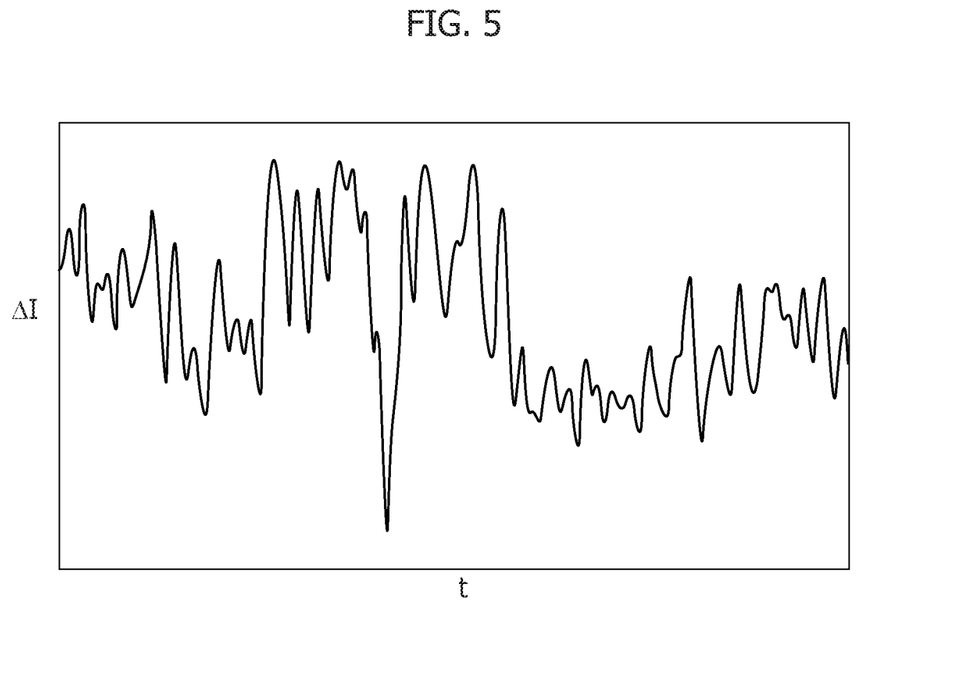
FIGS. 5 and 6 are exemplary time diagrams of signals as per the present disclosure.

FIG. 5 is exemplary of a relative variation signal $\Delta I$, e.g. obtained for the first landmark point 40.

In one or more embodiments, the third sub-stage 136 in the pre-processing stage 130 may comprise applying further processing, for instance time-series processing in order to obtain a relative variation $\Delta I$ of intensity value between subsequent frames, e.g. frame-by-frame, as exemplified in FIG. 5.

In one or more embodiments, the pre-processing stage 130 may be coupled to the ANN stage 140, providing the time-series 140, 142, $\Delta I$ of intensity of landmark points 40, 42, 400 of the face of the driver D extracted from the video recorded by the camera SP to the ANN stage 140.

As exemplified in FIG. 2, the training data collection stage 140T may receive from a photo-detector a signal from which a recorded sample of a PPG signal $P_t$, e.g. the sample $P_t$ having a limited and finite time duration, detected from the driver D may be processed via a dedicated pipeline, in ways per se known. FIG. 6 is exemplary of such a sample PPG signal $P_t$.

In one or more embodiments, a pipeline as disclosed in the Italian Patent Application No. 102017000081018 filed on Jul. 18, 2017 may be used in the training data collection stage 140T. In one or more embodiments, other methods for obtaining a recorded sample PPG signal $P_t$ may be employed.

In one or more embodiments, the sample PPG signal $P_t$ may be used for preliminary system calibration and/or for real-time continuous learning.

A method for training the ANN stage is discussed in the following, specifically with respect to FIG. 8.

In one or more embodiments, a multi-layer Long Short-Term Memory (briefly, LSTM) Artificial Neural Network (ANN) may be found suitable for use in the ANN stage 140.

As known to those of skill in the art (see, for instance, en.wikipedia.org/wiki/Long_short-term_memory) LSTM is a current designation applied to units in a recurrent neural network (RNN). A LSTM unit may be composed of a cell plus input, output and forget gates, with the cell able to remember values over arbitrary time intervals while the three gates regulate the flow of information into and out of the cell.

Figure 7A:
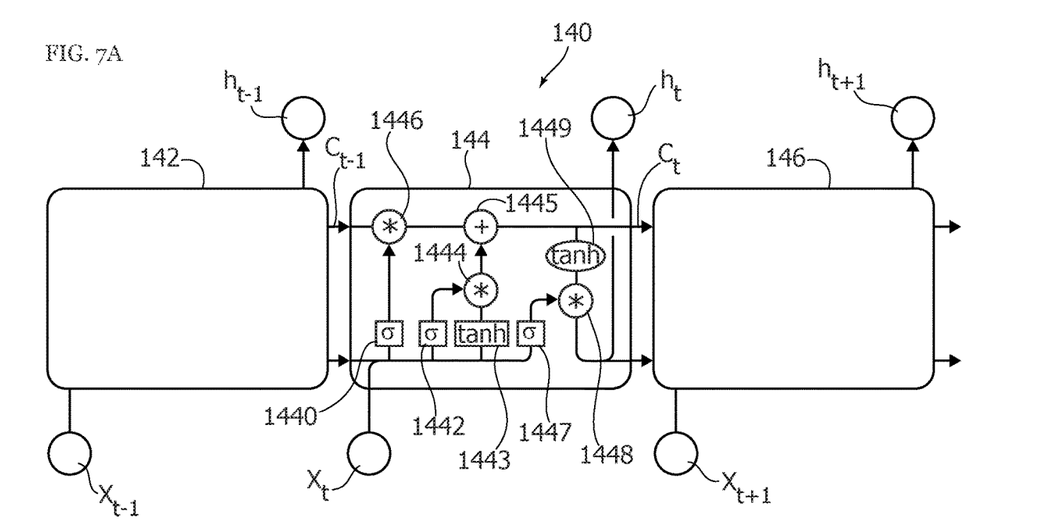
FIGS. 7A-7E are diagrams exemplary of an artificial neural network processing stage as per the present disclosure.
Figure 7B:
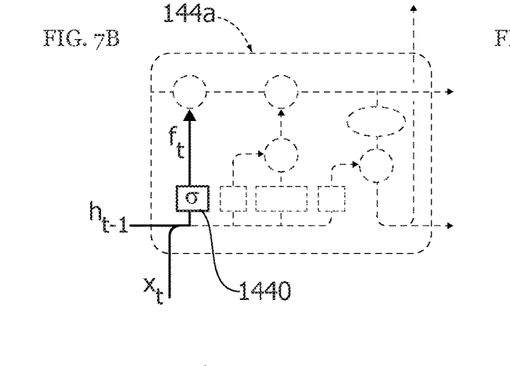
Figure 7C:
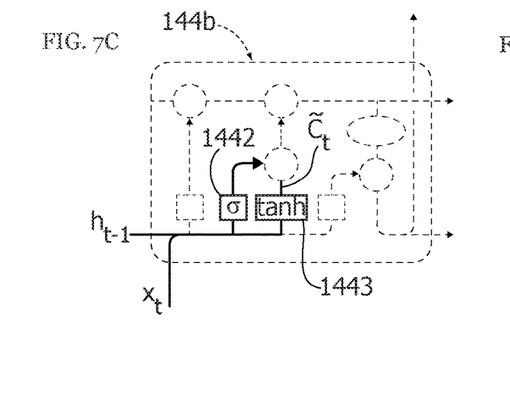

FIG. 7A is exemplary of a diagram of embodiments of a neural network architecture which may be used in the ANN stage 140, including for instance a plurality of LSTM neural network "neurons" or multi-layer units:

a first LSTM unit 142, configured to receive a first input $X_{t-1}$ and provide a first output $h_{t-1}$ and a first cell state $C_{t-1}$, a second LSTM unit 144, configured to receive a second input $X_t$ plus the first output $h_{t-1}$ of the first LSTM unit and provide a second output $h_t$ and a second cell state $C_t$, a third LSTM unit 146, configured to receive a third input $X_t$, plus the second output $h_t$ of the second LSTM and provide a third output $h_t$, and a third cell state $C_{t-1}$.

In one or more embodiments, the neural network units 142, 144, 146 may be chained in such a way that the output(s) of one unit go into the next one. Such an exemplary architecture may be extended to comprise any number of LSTM units, the discussed three stages being solely exemplary and in no way a limiting number.

FIGS. 7B to 7E are exemplary of the architecture and processing stages, also known as "gates" or "layers", which are employed in a single LSTM unit, for instance in the second unit 144.

In the following, for the sake of simplicity, principles underlying embodiments are discussed with respect to the second LSTM unit, being otherwise understood that such a discussion may be extended, mutatis mutandis, to any unit in the artificial neural network stage 140.

For instance, in the exemplary case considered, the second LSTM unit 144 may comprise a plurality of gates 144a, 144b, 144c, for instance:

a first gate 144a, also known as "forget gate", configured to receive the previous stage output $h_{t-1}$ and an input $x_t$, providing a combination $f_t$ of such received signals and configured to facilitate "forgetting" (e.g. discarding) irrelevant information, as discussed in the following;

a second gate 144b, configured to process the same signals received in the first gate 144a to obtain a bias value Ct, a third gate 144c, configured to provide an output value $h_t$.

In one or more embodiments, the first gate 144a may include a first sigmoid layer 1440, which may be used to facilitate the ANN stage 140 in "forgetting" information (e.g. outputting a zero) or "remembering" information (e.g. outputting an updated value $f_t$).

In one or more embodiments, the first sigmoid layer 1440 may process the second input $x_t$ and the first output $h_{t-1}$ so as to provide the combination $f_t$ which may be expressed as:

$$f_t = \sigma(W_f \cdot [h_{t-1}, x_t] + b_f)$$

where:

$W_f$ is a respective set of weights of the first gate 144a of the second LSTM unit 144.

$b_f$ is a respective set of bias values of the first gate 144a of the second LSTM unit 144. In one or more embodiments, the second gate 144b may include a set of layers 1442, 1443 and of coupled point-wise operations 1444, 1445, 1446. For instance, in the example considered, the set of layers 1442 includes a second sigmoid layer 1442 and a hyperbolic tangent layer 1443, as exemplified in FIG. 7C.

In the example considered, the second sigmoid layer 1442 processes the first output $h_{t-1}$ and the second input $x_t$ to provide a second combination $i_t$ which may be expressed as:

$$i_t = \sigma(W_i \cdot [h_{t-1}, x_t] + b_i)$$

where:

$W_i$ is a respective first sub-set of weights of the second gate 144b of the second LSTM unit 144, $b_i$ is a respective first sub-set of bias values of the second gate 144b of the second LSTM unit 144.

In the example considered, the hyperbolic tangent layer 1442 processes the first output $h_{t-1}$ and the second input $x_t$ to provide a third combination $\tilde{C}_t$ which may be expressed as:

$$\tilde{C}_t = \tanh(W_C \cdot [h_{t-1}, x_t] + b_i)$$

where:

$W_C$ is a respective second sub-set of weights of the second gate 144b of the second LSTM unit 144, $b_C$ is a respective second sub-set of bias values of the second gate 144b of the second LSTM unit 144.

Figure 7D:
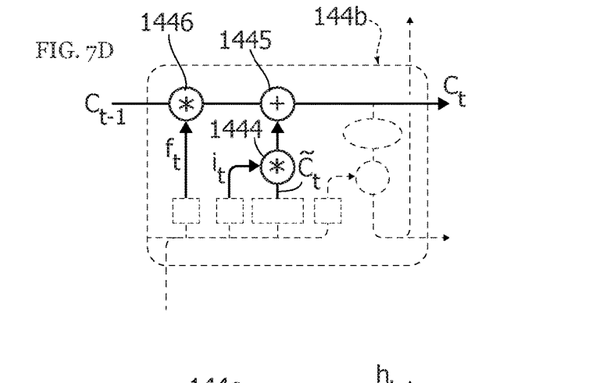

As exemplified in FIG. 7D, the set of point-wise operations may comprise scaling operations 1444, 1446 and adding operations 1445.

As a result, for instance, the second gate 144b may provide a second channel state value $C_t$ which may be expressed as:

$$C_t = f_t \cdot C_{t-1} + i_t \cdot \tilde{C}_t$$

where $f_t$, $C_{t-1}$, $i_t$ and $\tilde{C}_t$ are symbols indicating corresponding quantities discussed in the foregoing.

Figure 7E:
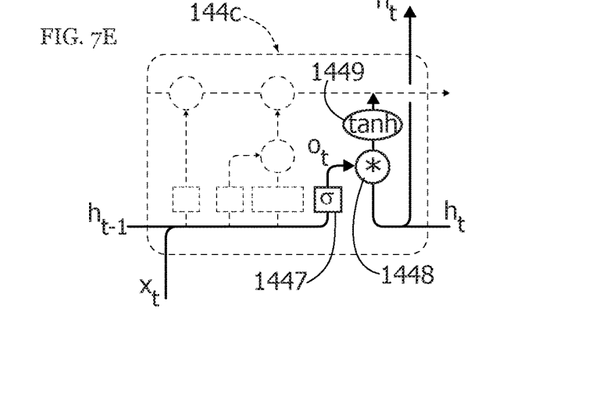

As exemplified in FIG. 7E, the third gate 144c may include a third sigmoid layer 1447, a third scaling operation 1448 and a hyperbolic tangent operation 1449.

In the example considered, for instance, the third gate 144c layer may select a cell state facilitating the ANN stage 140 to learn from long term dependency among input information.

For instance, the sigmoid layer may provide a third combination $o_t$ of second input $x_t$ and first output $h_{t-1}$ which may be expressed as:

$$o_t = \sigma(W_o \cdot [h_{t-1}, x_t] + b_o)$$

where:

$W_O$ is a respective third sub-set of weights of the third gate 144c of the second LSTM unit 144, $b_O$ is a respective third sub-set of bias values of the third gate 144c of the second LSTM unit 144.

As a result of further processing of the combination in the scaling 1448 and hyperbolic tangent 1449 operations, the third gate 144c may provide as output the third output value $h_t$ which may be expressed as:

$$h_t = o_t \cdot \tanh(C_t)$$

where $o_t$, $C_t$ are symbols indicating corresponding quantities discussed in the foregoing and tanh is the hyperbolic tangent function.

As mentioned, using LSTM units 142, 144, 146 in the ANN stage 140 may facilitate obtaining one or more embodiments of a model in which the model learns what information to store in long term memory and what to get rid of, hence providing a model which learns patterns in data which may be separate in time.

Figure 8:
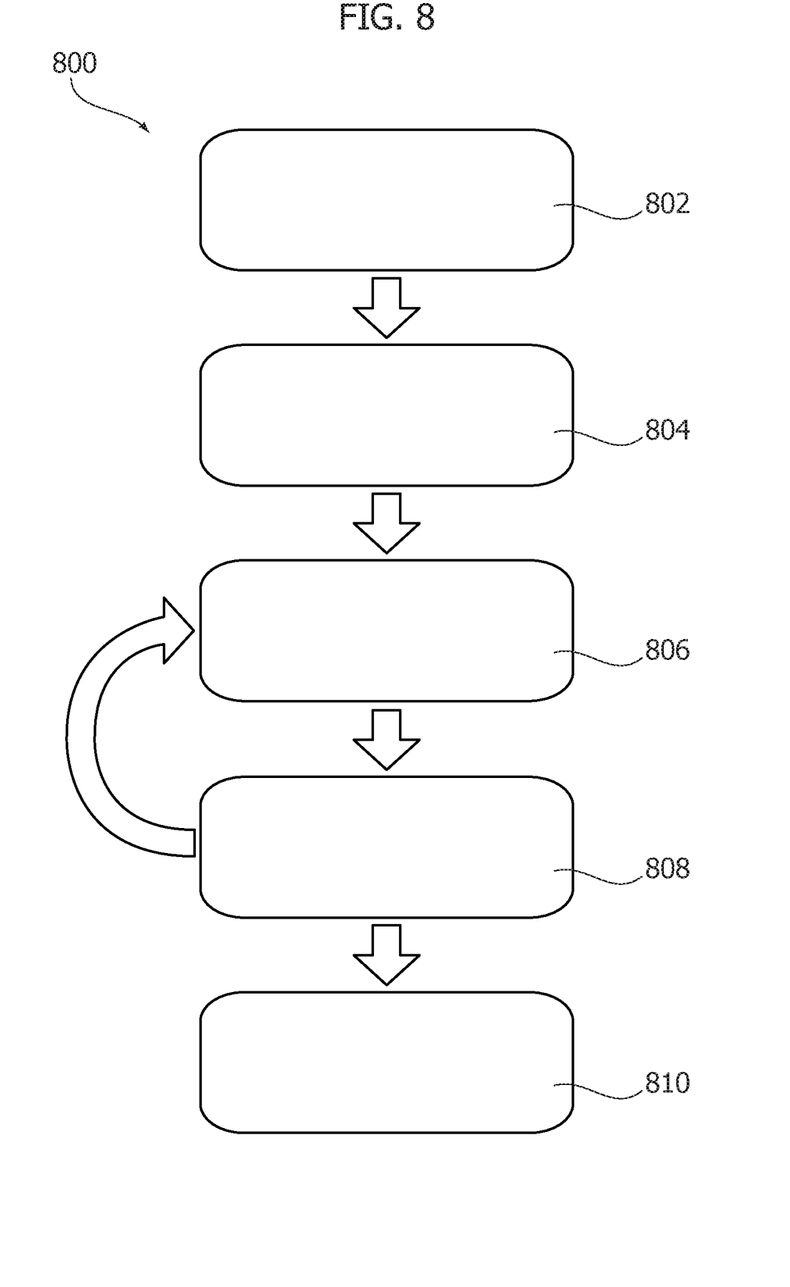
FIG. 8 is a diagram exemplary of operations in a method as per the present disclosure.

As mentioned, FIG. 8 is exemplary of a method 800 of "training" the ANN stage 140.

The purpose of the training 800 is to train an artificial intelligence system in order that this may learn the correlation between the sample PPG signal Pt and the signals indicative of respective landmark points 40, 42 intensity variation 140, 142 of the face of a vehicle driver D. Training 800 an artificial neural network processing stage 140 indicates operations aiming to set values for weight Wf, Wi, WC, WO and bias bf, bi, bc, bO in respective gates/layers 144a, 144b, 144c in respective units 142, 144, 146 of the ANN stage 140.

In one or more embodiments, training of the neural network is of the supervised type. A learning target can thus be provided, e.g. in the form of the result the network is expected to provide if a certain PPG pattern is applied as an input. The target/output set can thus be represented by a corresponding reconstructed PPG pattern PPG_rec (that is, corresponding to the PPG pattern applied to the input).

In the example considered, the training method 800 may comprise:

providing 802 a sample PPG signal Pt, e.g. acquired via photo-detector sensors PD in a steering wheel and/or stored in the training collection stage 140T or other PPG sensing circuitry configured for sensing the sample set of PPG signals (Pt) over a given time duration indicative of heart pulsatile activity occurring with a variable heart rate, the PPG sensing circuitry PD configured to be disabled at the expiry of a given time duration, setting 804 as goal for the ANN stage 140 to provide an output signal PPG_rec as close as possible, e.g. ideally completely matched, to the sample PPG signal Pt included in the training set 140T, applying 806 artificial neural network processing 140 to the time-series 140, 142 in order to train the artificial neural network to learn a correlation between the time-series and the PPG patterns, e.g. providing a reconstructed PPG signal PPG_rec which during the training phase is targeted to have a same pattern of the input PPG sample Pt;

evaluating the training 808 by an evaluation parameter, e.g. by comparing the distance between adjacent minimum points in the reconstructed PPG signal PPG_rec and in the sample PPG Pt and/or measuring the correlation between FFT spectra of the sample PPG signal Pt minimum points versus the reconstructed PPG signal PPG_rec minimum points;

iterating 810 the training procedure steps from applying ANN processing 806 to evaluating the training 808 for instance either for a fixed number of times, e.g. three epochs, or as long as the evaluation parameter is below or above a desired threshold, e.g. in the example considered until the distance between adjacent minimum points in the reconstructed PPG signal PPG_rec and in the sample PPG Pt is above a desired value.

In one or more embodiments, once the training phase 800 is performed, the ANN stage 140 receives as input time-series 140, 142 provided by the pre-processing stage 130 and may be capable to reconstruct a respective reconstructed PPG signal PPG_rec exploiting the correlation among signal patterns learnt during the training phase 800. Dedicated tests have shown that a method as discussed herein may reach a 93% accuracy in detecting the state of the driver, for instance when in a drowsy or wakeful stage.

In one or more embodiments, corresponding PPG signals PPG_rec may thus be reconstructed in the neural network processing stage 140 to be supplied to a post-processing stage 150, configured to produce an HRV estimation value, e.g. from the minimum points peak of the reconstructed PPG signals, an estimate of the HRV signal in turn adapted to produce a driver level of attention/drowsiness signal A.

Such a signal may be reflected e.g. by an alert A (e.g. sound and/or visual alert) to the drivers and/or control of the vehicle being taken over by an advanced driver-assistance systems (ADAS).

One or more embodiments, may be installed on board a vehicle V for driving by a driver D wherein the recorded images (and PPG signals) are indicative of the pulsatile activity of the heart of the vehicle driver and the indicator A estimated from heart rate variability, HRV, is indicative of, e.g., the driver D being in a drowsy state.

In one or more embodiments, an act of evaluating the "goodness" of the training 808 may also be performed in a parallel second ANN processing stage, as exemplified in FIG. 8.

In one or more embodiments, the LTSM learning algorithm will enable the ANN stage 140 to learn the model which "maps" the intensity variation signals at landmarks (for a certain driver) onto the PPG signal, e.g. for the same driver.

It is observed that, at least under certain circumstances, such a network may not reconstruct adequately a mathematical model for the landmarks time-series to PPG mapping.

Specifically, it is found that the ANN stage 140 may provide a shape correspondence which makes it possible to obtain a PPG signal reconstructed from the image landmarks which can be superposed in terms of "pattern/shape" over a desired result without however exhibiting a degree of reliability which may permit to use it as a "robust" PPG in producing the HRV evaluation.

Stated otherwise, at least under certain circumstances, the result obtainable from the ANN stage 140 may not exhibit precision and robustness as desirable for a PPG signal PPG_rec intended to be used for computing a HRV index, e.g. for drowsiness estimation.

For that reason, in one or more embodiments another neural network of a different type may be used in parallel to the ANN stage 140, e.g. as a backup.

Such a parallel second ANN processing stage may receive the video signal from the camera SP and apply Convolutional Neural Network (briefly, CNN) to the images, facilitating to classify images of face features of the driver D and to detect whether the driver D is in a wakeful or drowsy state.

Dedicated tests have shown that the CNN layer may correctly identify the driver's attention state, e.g. with an accuracy level between 80% and 90%. For instance, a portion of a face of a driver D may be supplied to the CNN stage, which may consequently label it with the known state of the person when the picture was taken and/or with the label provided as output by the CNN stage.

In one or more embodiments, training the ANN stage 140 may hence comprise collecting images of eye portions of face images of individuals in two different attention states (e.g., drowsy/wakeful, respectively), providing the images to the first ANN stage and evaluating the output indicator provided as matching the known state (drowsy/wakeful), and iterating training until a desired accuracy is reached.

A method according to embodiments may comprise:

receiving (for instance, 130) a video signal, comprising a time series of images of a face of a human, wherein the images in the time series of images comprise a set of landmark points (for instance, 40, 42) in the face (for instance, 400);

applying to the video signal tracking processing (for instance, 132) to reveal variations over time of at least one image parameter at the set of landmark points in the human face and generating (for instance, 134, 136) a set of variation signals (for instance, 140, 142) indicative of variations revealed at respective landmark points in the set of landmark points the variation signals being indicative of heart pulsatile activity occurring with a variable heart rate;

applying to the set of variation signals, processing (for instance, 140) comprising artificial neural network processing (for instance, 142, 144, 146) to produce a reconstructed PhotoPletysmoGraphy, PPG, signal (for instance, PPG_rec); and estimating (for instance, 150) a heart rate variability, HRV, of a variable heart rate of the human as a function of the reconstructed PPG signal.

In one or more embodiments, artificial neural network processing of the set of variation signals may comprise Long Short-Term Memory, LSTM, processing (for instance, 144a, 144b, 144c).

One or more embodiments may comprise calculating a driver attention level indicator (for instance, A) from the estimated heart rate variability, HRV.

In one or more embodiments the method may be implemented on board a vehicle (for instance, V) driven by a driver (for instance, D), wherein the video signal received comprises a time series of images of the face of the driver, wherein the video signal is indicative of the pulsatile activity of the heart of the driver and the driver attention level indicator is indicative of drowsiness of the driver.

One or more embodiments may comprise, as a function of the driver attention level indicator, at least one of issuing a drowsiness alert to the vehicle driver, and/or causing a driver assistance system to take over control of the vehicle.

In one or more embodiments, generating the set of reconstructed PPG signals via artificial neural network processing of the set of signals may comprise training (for instance, Boo) at least one artificial neural network over a training set of signals (for instance, 140T) produced during sampling (for instance, PD) a sample set of PPG signals (for instance, Pt), wherein the training comprises reducing mismatch between the set of reconstructed signals and the sample set of PPG signals, preferably mismatch between minimum points of respective signals.

In one or more embodiments, applying to the set of variation signals processing comprises obtaining a relative variation (for instance, ΔI) of the at least one image parameter between subsequent images in the video signal.

A system according to one or more embodiments may comprise:

a video-recording device (for instance, SP) for recording a video signal comprising a time series of images of a face of a human, wherein the images in the time series of images comprise a set of landmark points in the face;

processing circuitry (for instance, 100) coupled to the video-recording device to receive the video signal therefrom, the processing circuitry comprising artificial neural network processing circuits (for instance, 142, 144, 146) and configured for estimating (for instance, 150) heart rate variability, HRV, of a variable heart rate as a function of the reconstructed set of PPG signals (for instance, PPG_rec) with the method according to one or more embodiments.

One or more embodiments may comprise PPG sensing circuitry (for instance, PD) configured for sensing a sample set of PPG signals (for instance, Pt) included in the training set of signals (for instance, 140T), the sample set of PPG signals sensed over a given time duration indicative of heart pulsatile activity occurring with a variable heart rate, the PPG sensing circuitry configured to be disabled at the expiry of a given time duration.

In one or more embodiments, the video-recording device for recording the video signal may be a smart-phone comprising at least one camera, preferably comprising a low frame-rate camera.

A vehicle according to one or more embodiments may be equipped with a system according to one or more embodiments in combination with at least one driver assistance device (for instance, A), the driver assistance device configured to operate as a function of the estimated heart rate variability, HRV.

One or more embodiments may comprise a computer program product loadable in the memory of at least one processing circuit (for instance, 100) and including software code portions for executing the steps of the method according to one or more embodiments when the product is run on at least one processing circuit.

It will be otherwise understood that the various individual implementing options exemplified throughout the figures accompanying this description are not necessarily intended to be adopted in the same combinations exemplified in the figures. One or more embodiments may thus adopt these (otherwise non-mandatory) options individually and/or in different combinations with respect to the combination exemplified in the accompanying figures.

Without prejudice to the underlying principles, the details and embodiments may vary, even significantly, with respect to what has been described by way of example only, without departing from the extent of protection. The extent of protection is defined by the annexed claims.

What is claimed is:

1. A method, comprising:
   receiving a video signal that comprises a time series of images of a face of a human, wherein the images in the time series of images comprise a set of landmark points in the face;
   applying tracking processing to the video signal to reveal variations over time of at least one image parameter at the set of landmark points in the human face;
   generating a set of variation signals indicative of variations revealed at respective landmark points in the set of landmark points, the set of variation signals being indicative of heart pulsatile activity occurring with a variable heart rate;
   applying processing to the set of variation signals, the processing comprising artificial neural network processing to produce a reconstructed PhotoPletysmoGraphy (PPG) signal, wherein applying the processing to the set of variation signals comprises training at least one artificial neural network over a training set of signals produced while sampling a sample set of PPG signals, wherein the training comprises reducing mismatch between a set of reconstructed signals and the sample set of PPG signals; and
   estimating a heart rate variability of a variable heart rate of the human as a function of the reconstructed PPG signal.

2. The method of claim 1, wherein the artificial neural network processing of the set of variation signals comprises long short-term memory processing.

3. The method of claim 1, further comprising calculating a driver attention level indicator from the estimated heart rate variability.

4. The method of claim 3, wherein the method is implemented on board a vehicle driven by a driver and wherein the video signal received comprises a time series of images of the face of the driver.

5. The method of claim 4, wherein the video signal is indicative of the heart pulsatile activity of the heart of the driver and the driver attention level indicator is indicative of drowsiness of the driver.

6. The method of claim 5, further comprising issuing a drowsiness alert to the driver as a function of the driver attention level indicator.

7. The method of claim 5, further comprising causing a driver assistance system to take over control of the vehicle as a function of the driver attention level indicator.

8. The method of claim 1, wherein reducing the mismatch comprises reducing the mismatch between minimum points of respective signals.

9. The method of claim 1, wherein applying processing to the set of variation signals, processing comprises obtaining a relative variation of the at least one image parameter between subsequent images in the video signal.

10. A non-transitory storage medium storing a computer program loadable in a memory of at least one processing circuit, the computer program including software code for executing the steps of the method of claim 1 when executed by at least one processing circuit.

11. A system, comprising:
a video-recording device configured to record a video signal that comprises a time series of images of a face of a human, wherein the images in the time series of images comprise a set of landmark points in the face; and
processing circuitry coupled to the video-recording device to receive the video signal therefrom, the processing circuitry comprising artificial neural network processing circuits and being configured to estimate heart rate variability of a variable heart rate as a function of a reconstructed PhotoPletysmoGraphy (PPG) signal by applying tracking processing to the video signal to reveal variations over time of at least one image parameter at the set of landmark points in the human face, generating a set of variation signals indicative of variations revealed at respective landmark points in the set of landmark points, the set of variation signals being indicative of heart pulsatile activity occurring with a variable heart rate, applying artificial neural network processing to the set of variation signals to produce the reconstructed PPG signal, and estimating a heart rate variability of a variable heart rate of the human as a function of the reconstructed PPG signal, wherein applying the artificial neural network processing comprises training at least one artificial neural network using a training set of signals, wherein the training comprises reducing mismatch between a set of reconstructed signals produced by the artificial neural network during the training and a sample set of PPG signals corresponding to the training set of signals.

12. The system of claim 11, comprising PPG sensing circuitry configured to sense the sample set of PPG signals included in the training set of signals, the sample set of PPG signals sensed over a given time duration indicative of heart pulsatile activity occurring with a variable heart rate, the PPG sensing circuitry configured to be disabled at the expiry of a given time duration.

13. The system of claim 12, wherein the video-recording device for recording the video signal is a smart-phone comprising a camera.

14. The system of claim 13, wherein the camera comprises a low frame-rate camera.

15. The system of claim 11, wherein the system is installed in a vehicle with a driver assistance device that is configured to operate as a function of the estimated heart rate variability.

16. The system of claim 11, wherein the processing circuitry is further configured to calculate, based on the reconstructed PPG signal, an indicator indicative of drowsiness of the human.

17. A system, comprising:
a video-recording device configured to record a video signal that comprises a time series of images of a face of a human, wherein the images in the time series of images comprise a set of landmark points in the face;
processing circuitry; and
a non-transitory storage medium storing a computer program that includes software code that, when executed by the processing circuitry, causes the processing circuitry to perform a method comprising:
applying tracking processing to the video signal to reveal variations over time of at least one image parameter at the set of landmark points in the human face;
generating a set of variation signals indicative of variations revealed at respective landmark points in the set of landmark points, the variation signals being indicative of heart pulsatile activity occurring with a variable heart rate;
applying processing to the set of variation signals, the processing comprising artificial neural network processing to produce a reconstructed PhotoPletysmoGraphy (PPG) signal, wherein applying the processing to the set of variation signals comprises training an artificial neural network using a training set of signals, wherein the training comprises reducing mismatch between a set of reconstructed signals produced by the artificial neural network during the training and a sample set of PPG signals corresponding to the training set of signals; and
estimating a heart rate variability of a variable heart rate of the human as a function of the reconstructed PPG signal.

18. The system of claim 17, wherein the artificial neural network processing of the set of variation signals comprises long short-term memory processing.

19. The system of claim 17, further comprising calculating a driver attention level indicator from the estimated heart rate variability.

20. The system of claim 17, wherein applying processing to the set of variation signals, processing comprises obtaining a relative variation of the at least one image parameter between subsequent images in the video signal.

* * * * *